United States Patent [19]

Kerrigan et al.

[11] Patent Number: 5,563,317
[45] Date of Patent: *Oct. 8, 1996

[54] METHOD FOR THE PRODUCTION OF HIGH PROPORTIONS OF HOMOKARYONS IN BREEDING STOCK OF THE MUSHROOM *AGARICUS BISPORUS*

[75] Inventors: Richard W. Kerrigan, Worthington; Mark C. Spear, Cabot, both of Pa.

[73] Assignee: Sylvan Spawn Laboratory Incorporated, Kittanning, Pa.

[*] Notice: The term of this patent shall not extend beyond the expiration date of Pat. No. 5,304,721.

[21] Appl. No.: 196,139

[22] PCT Filed: Jun. 18, 1993

[86] PCT No.: PCT/US93/05874

§ 371 Date: Feb. 16, 1994

§ 102(e) Date: Feb. 16, 1994

[87] PCT Pub. No.: WO94/00006

PCT Pub. Date: Jan. 6, 1994

Related U.S. Application Data

[63] Continuation of Ser. No. 900,546, Jun. 18, 1992, Pat. No. 5,304,721.
[51] Int. Cl.$^6$ ............................. A01H 15/00; A01H 1/00
[52] U.S. Cl. .................... 800/200; 800/DIG. 8; 47/1.1; 47/58; 47/DIG. 1
[58] Field of Search ............................. 800/200, DIG. 8; 435/172.3; 47/1.1, DIG. 1, 58

[56] References Cited

PUBLICATIONS

Raper et al (1972) Mycologia 64: 1088–1117.

*Primary Examiner*—Douglas W. Robinson
*Assistant Examiner*—Elizabeth F. McElwain
*Attorney, Agent, or Firm*—Renner, Kenner, Greive, Bobak, Taylor & Weber

[57] ABSTRACT

A method for the production of high proportions of homokaryons among spores from breeding stock of the mushroom *Agaricus bisporus* includes the steps of providing a first strain of *Agaricus bisporus* having tetrasporic ancestry and which carries a gene or genes that determines the trait for production of basidia which predominantly bear at least three spores rather than two, and crossing the first strain of *Agaricus bisporus* with a second, different strain of *Agaricus bisporus* to form at least one hybrid heterokaryotic culture. The culture is capable of producing mushrooms having basidia which predominately bear at least three spores, many of which are homokaryotic. The homokaryons taken from the homokaryotic spores can be used in crosses to produce new hybrid strains of *Agaricus bisporus* mushrooms which may exhibit improvements with respect to various traits including productivity, rate of development, disease resistance, aesthetic qualities and the like. Also, the homokaryons can be used to map genes that control phenotypic traits of interest.

10 Claims, No Drawings

METHOD FOR THE PRODUCTION OF HIGH PROPORTIONS OF HOMOKARYONS IN BREEDING STOCK OF THE MUSHROOM *AGARICUS BISPORUS*

This application is a 371 of PCT/US93/05874 filed Jun. 18, 1993, which is a continuing case of U.S. Ser. No. 07/900,456 filed Jun. 18, 1992, now U.S. Pat. 5,304,721.

TECHNICAL FIELD

This invention relates to the production and improvement of mushrooms, the sporocarps of edible agaric fungi. More particularly, this invention relates to the method of production of, and the utilization of, high proportions of homokaryons in hybrid breeding stock of the mushroom species *Agaricus bisporus* (Lange) Imbach, strains of which are commercially cultivated. Specifically, this invention relates to the introduction of a heritable elevated basidial spore number trait into stocks of *Agaricus bisporus* mushrooms, by producing hybrid *Agaricus bisporus* mushrooms which carry and express the trait and which produce relatively large percentages or fractions of homokaryons that may be easily recovered from among the offspring of the hybrid strains. These homokaryons can be used in crosses to produce new hybrid strains of *Agaricus bisporus* mushrooms which may exhibit improvements with respect to various traits including productivity, rate of development, disease resistance, aesthetic qualities and the like. Also, these homokaryons can be used to map genes that control phenotypic traits of economic importance.

BACKGROUND OF THE INVENTION

The mushroom species *Agaricus bisporus* (Lange) Imbach, also known as *Agaricus brunnescens* Peck, is a well known and widely cultivated commercial mushroom. At least one distinct horticultural variety, i.e., cultivated strain, of this species of mushroom has been the subject of a U.S. Plant Patent, No. Plant 7,636, incorporated herein by reference.

Notably, a distinctive characteristic of *Agaricus bisporus*, that historically has defined the species, is that virtually all previously known strains have predominantly produced only two spores on each basidium. Generally, only small percentages (less than 10 percent) of basidia having more than two spores have been shown to occur in various *Agaricus bisporus* strains. In very rare instances, laboratory strains derived from predominantly bisporic strains have been reported to exhibit basidia in which basidia bearing more than two spores may predominate. These reports appear to involve traits which are either (1) unstable or inconsistently expressed, (2) possible artifacts of the sampling method (mushrooms too immature to provide representative data), or (3) associated with aberrant gross sporocarp morphologies which are unsuitable for the commercial market. In any event, although a long-felt need exists for increasing the production of homokaryons in breeding stock of *Agaricus bisporus*, none of the foregoing reports have led to a useful method for addressing this need.

The characteristic of producing only two spores on each basidium is disadvantageous to the mushroom breeder. Following meiosis in a typical two-spored basidium of *Agaricus bisporus*, each spore receives two nuclei which are jointly necessary for fertility. As a result, most spores of this species of mushroom, as historically known, produce fertile, heterokaryotic progeny. Such a trait of self-fertility poses a problem for the mushroom breeder because heterokaryons apparently undergo little, if any, hybridization. The bisporic trait characterizes all commercially cultivated strains as well as the great majority of naturally occurring or "wild" strains of *Agaricus bisporus* thus far discovered.

In contrast, all other known species of Agaricus produce predominantly fourspored basidia. In most agaric fungi, tetrasporic basidia are usually associated with the production of mononucleate homokaryotic spores which germinate to produce infertile homokaryons. In mushroom breeding, homokaryons, haploid strains which function in a manner similar to the gameres of plants and animals, are generally required for the practical crossbreeding of stocks to produce new hybrid strains. Homokaryons mate easily with other compatible homokaryons. However, less conventionally, it is sometimes possible to cross a homokaryon and a heterokaryon or, in some instances, to cross two heterokaryons.

To produce hybrids in the conventional manner, homokaryons such as those obtained from the homokaryotic spores of the parent varieties of mushrooms must fuse and establish a common heterokaryotic cytoplasm. However, homokaryons are presently very difficult to obtain by conventional spore isolation from the two-spored *Agaricus bisporus* strains because typically less than three percent of the spores produced by such strains are homokaryotic. The great majority of spores of these strains produce fertile, heterokaryotic progeny as noted hereinabove.

Moreover, heterokaryotic and homokaryotic offspring are generally indistinguishable from one another except by genetic screening, such as by the use of allozyme or DNA markers, which is time consuming and costly. Homokaryons are also difficult to obtain by other presently available methods. For a more complete description of some conventional methodologies for the recovery of *Agaricus bisporus* homokaryons, and some difficulties and drawbacks thereof, see "Strategies For The Efficient Recovery of *Agaricus bisporus* Homokaryons" by Kerrigan et al. in *Mycologia*, 84(4), 575–579 (1992), hereby incorporated by reference.

In order to overcome the difficulties associated with obtaining homokaryons from the two-spored *Agaricus bisporus* strains, attempts have been made to interbreed a four-spored strain from another known species of Agaricus with a two-spored strain of *Agaricus bisporus*. For example, in Raper, "Sexuality and Life Cycle of the Edible, Wild *Agaricus bitorquis*," Journal of General Microbiology, 95, 54–66 (1976) a homokaryon from the species *Agaricus bitorquis* was crossed with a homokaryon from the species *Agaricus bisporus*. However, Raper was unable to establish stable, fertile heterokaryons, and thus, was precluded from cross-breeding. In fact, no attempt to interbreed a four-spored species of Agaricus with a two-spored *Agaricus bisporus* has ever been successful. Accordingly, heretofore, any very highly four-spored strain of Agaricus was believed not to belong to the species *Agaricus bisporus* and was believed not capable of interbreeding with the species *Agaricus bisporus*.

Nevertheless, the need has remained for a process which will permit the mushroom breeder to obtain relatively large percentages or fractions of homokaryons relatively quickly, efficiently and inexpensively from the breeding stock of the *Agaricus bisporus* mushroom. Moreover, the mushroom breeder has always strived to increase the mushroom productivity yield and to shorten the duration of the mushroom crop cycle. A crop of mushrooms which are higher yielding and earlier fruiting than most commercial mushrooms would be economically desirable.

SUMMARY OF INVENTION

It is, therefore, an object of the present invention to provide a method for producing relatively high proportions of homokaryons from the breeding stock of the cultivated mushroom species *Agaricus bisporus*.

It is another object of the present invention to provide a method, as above, which is less costly and more efficient than the present methods for producing and screening for homokaryons from breeding stocks of this particular species of mushroom.

It is a further object of the present invention to provide a method for introducing an elevated basidial spore number trait into the bisporic stocks of *Agaricus bisporus*.

It is still another object of the present invention to provide a method, as above, which will produce homokaryons of *Agaricus bisporus* which are useful for mapping genes that control phenotypic traits of economic importance.

It is yet another object of the present invention to provide a method, as above, which would produce a higher yielding and earlier fruiting crop of *Agaricus bisporus* mushrooms.

These and other objects of the present invention, together with the advantages thereof over known methods, which shall become apparent from the description which follows, are accomplished by the invention as hereinafter described and claimed.

In general, the present invention provides a method for the production of homokaryons from breeding stock of the mushroom *Agaricus bisporus* which includes the steps of providing a first strain of *Agaricus bisporus* having tetrasporic ancestry and which carries at least one gene that determines a trait for production of basidia which predominantly bear at least three spores, and crossing the first strain with at least a second strain of *Agaricus bisporus* to form at least one hybrid heterokaryotic culture. At least one hybrid heterokaryotic culture is capable of producing mushrooms having basidia which predominantly bear at least three spores, a fraction of the spores being homokaryotic.

The present invention also provides a method for introducing a trait for the production of basidia which predominantly bear at least three spores into stocks of the mushroom *Agaricus bisporus* which includes the steps of providing a first strain, from a first stock of *Agaricus bisporus*, having tetrasporic ancestry and which carries at least one gene which determines the trait for production of basidia which predominantly bear at least three spores, and incorporating the gene or genes into the genetic background of at least a second strain, from a second stock of *Agaricus bisporus*, such that the new resultant stock combines characteristics of the second stock with the trait.

The present invention also provides for homokaryons produced from spores on hybrid mushrooms and their descendants, the hybrid mushrooms being formed by providing a first strain of *Agaricus bisporus* having tetrasporic ancestry and which carries at least one gene that determines a trait for production of basidia which predominantly bear at least three spores, and crossing the first strain with at least a second strain of *Agaricus bisporus* to form at least one hybrid heterokaryotic culture which is capable of producing the hybrid mushrooms and their descendants.

The present invention further provides for heterokaryons, and their inbred and outcrossed descendants, produced from a cross between at least two strains of *Agaricus bisporus*, at least one of the strains having tetrasporic ancestry and carrying at least one gene which determines a trait for production of basidia which predominantly bear at least three spores.

Still further, the present invention provides a method for selectively introducing an elevated basidial spore number trait into stocks of *Agaricus bisporus* including the steps of mapping a gene locus which determines the elevated basidial spore number traits; cloning an allele of the gene locus, which causes expression of the elevated basidial spore number trait, from a strain of *Agaricus bisporus* having tetrasporic ancestry; incorporating a DNA sequence encoding the allele into a nucleic acid vector construct; and introducing the vector construct into the cytoplasm of a recipient strain of *Agaricus bisporus*.

The present invention also provides a method for mapping gene loci in the nuclear genome of a hybrid strain of *Agaricus bisporus* which is heterozygous for at least one trait-determining locus, and which expresses an elevated basidial spore number trait, including the steps of isolating a sufficient number of homokaryon cultures from spores obtained from mushrooms produced by the hybrid strain; characterizing the homokaryons with respect to the presence of a trait of interest; further characterizing the genotypes of the homokaryons using genetic markers; and analyzing the results of the characterizations for joint versus independent segregation.

Finally, the present invention provides a method for predicting the inheritance in homokaryotic offspring of alleles at a first locus, the locus selected from the group consisting of MAT and SNT, including the step of determining the genotype of the homokaryon at least one other different locus, the different locus selected from the group consisting of MAT, SNT, PEP1, PEP2, R4-1, R4-3, P1N17, P1N31, P1, N148, P1N150, P33N25-11, P33N25-4 and R18-6.

PREFERRED EMBODIMENT FOR CARRYING OUT THE INVENTION

The production of homokaryotic offspring from both wild and cultivated, two-spored breeding stock of the commercial mushroom *Agaricus bisporus* has always been time consuming and costly. This species of mushroom, as historically known, characteristically predominantly produces two-spored basidia. Thus, the resultant offspring from the spores are mostly, and sometimes always, heterokaryotic. Consequently, much effort and expense is associated with testing, either genetically or otherwise, to determine which of the spores of each mushroom are homokaryotic and which are heterokaryotic. For example, research experience indicates that, on average, it generally takes a researcher one to two days of effort to obtain a single homokaryon using conventional random spore isolation methods followed by genetic screening. Even greater effort and expense may be associated with obtaining homokaryons by alternative means such as microsurgery or protoplast production.

The present invention provides a novel method for obtaining homokaryons of *Agaricus bisporus* by producing new hybrid strains, each of which results from the cross of a first strain of *Agaricus bisporus* having tetrasporic ancestry with at least a second strain of *Agaricus bisporus*. By the term "tetrasporic ancestry", it is meant that the strain is genealogically descended from a strain belonging to a taxonomic variety of *Agaricus bisporus* which produces mushrooms characteristically having predominantly tetrasporic basidia. One such tetrasporic taxonomic variety is the rare, recently discovered *Agaricus bisporus* var. *burnettii*. In contrast, *Agaricus bisporus* var. bisporus, which encompasses all historically known strains of *Agaricus bisporus*, is characterized by mushrooms which typically produce predominantly two-spored basidia. The term "genealogically descended" is specifically intended to distinguish this relationship from evolutionary descent, i.e., a naturally occurring process of genetic divergence typically involving at least hundreds of generations or thousands of years.

These first-generation hybrid strains have basidia which, without any known exception, predominantly bear at least three spores, a relatively large fraction of these spores being homokaryotic. As such, these strains produce homokaryons in higher proportions than what exists in today's two-spored commercial strains. It is meant by the terms "large fraction" and "higher proportions" as well as "high proportions" as noted in the title of the invention, a fraction or percentage of spores and/or homokaryons greater than the 0 to about 10 percent that is typically observed in the two-spored variety, *Agaricus bisporus* var. *bisporus*. Generally, in hybrids containing the elevated basidial spore number trait, this percentage is above about 10 percent and has been observed to exceed about 50 percent as shown hereinbelow. Moreover, the theoretical limit approaches 100 percent.

With respect to the present invention, it has been found that such hybrids can be produced because the homokaryons of the four-spored var. *burnettii* of *Agaricus bisporus* will interbreed freely with homokaryons of both wild and cultivated strains of the two-spored var. *bisporus* of *Agaricus bisporus* when conventional crossbreeding techniques are used. Thus, hybrids combining the desirable genetic background of the traditional breeding stocks of *Agaricus bisporus* var. *bisporus* with the gene or genes that confer the elevated basidial spore number trait found in strains of or descended from strains of *Agaricus bisporus* var. *burnettii* may be formed. By the term "elevated basidial spore number", it is meant that a relatively larger number of basidia, relative to the bisporic variety, or a bisporic progenitor, have more than two spores. Even more significantly, when these hybrids are induced to produce mushrooms, for example, following transfers to grain medium and compost medium, the hybrid mushrooms have basidia which predominantly bear three or more spores, most of which are homokaryotic.

The reason the elevated basidial spore number trait results in a high proportion of homokaryotic offspring is thought to be that the four post-meiotic nuclei tend to migrate singly into the four spores of a tetrasporic basidium. Therefore, each new spore is typically mononucleate and homokaryotic. A three-spored basidium may produce two homokaryotic spores and one binucleate, heterokaryotic spore, or three homokaryotic spores. Homokaryotic strains germinate to produce homokaryotic isolates (homokaryons).

Because first-generation intervarietal hybrids always express the elevated basidial spore number trait, the trait must therefore exhibit genetic dominance. Thus, a hybrid strain of *Agaricus bisporus* which carries the trait for the production of basidia which predominantly bear at least three spores, i.e, the elevated basidia spore number trait, will itself produce relatively large fractions of homokaryotic offspring which can be used to produce further hybrid descendants. The dominance of this trait is of great practical value, since in the case of a recessive trait, most carriers, including all first generation intervarietal hybrids, would not express the trait.

This trait can be passed down to all generations of descendants. The percentage of hybrid homokaryotic offspring that will carry the gene or genes for the elevated basidial spore number trait will depend upon the number of genetic loci involved (present evidence indicates that only one locus has a major effect in determining basidial spore number) and upon whether the hybrid receives copies of any allele of such a gene responsible for the elevated basidial spore number trait from both, one or neither parents. By selecting homokaryotic offspring of hybrids on the basis of whether they carry any allele responsible for the elevated basidial spore number trait or not, it is then possible to design and produce at will subsequent generations of hybrids which exhibit one of the three following behaviors: (i) elevated basidial spore number (typically, trisporic or tetrasporic) hybrids whose direct descendants will all carry and express the elevated basidial spore number trait, (ii) elevated basidial spore number hybrids whose direct descendants will show segregation for two-spored and elevated basidia spore number traits, and (iii) two-spored hybrids whose offspring carry only the two-spored trait. Furthermore, through repeated back-crossing, using appropriate hybrid homokaryotic offspring, a gene determining the elevated basidial spore number trait can be incorporated independently within the genetic background of any traditional two-spored breeding stock.

A preferred technique to produce hybrid heterokaryons of *Agaricus bisporus* is to transfer inoculum of each of two substantially pure cultures of homokaryons to a suitable medium, for example, agar media such as potato dextrose agar (PDA) or complete yeast medium agar (CYMA). The inocula are placed about 1 to 2 centimeters apart. The colonies that grow from the inocula are allowed to grow until a junction zone of extensive contact along the opposing margins of the two colonies has occurred. Mating between sexually compatible homokaryons occurs via cell-fusion and the formation of common or shared cytoplasm. Fluffy or strandy mycelium is sometimes seen at this point in compatible crosses. Inoculum from the junction zone of successful crosses, which will contain newly heterokaryotic hybrid mycelium, is then transferred to a fresh medium to establish a heterokaryotic culture. On this latter culture, tests to confirm heterokaryosis, which indicates a successful cross, may subsequently be performed. Heterokaryosis can be determined by genetic evaluation, demonstration of fertility or comparable methodologies.

Once the elevated spore number trait has been incorporated into breeding stock, it becomes easier to manipulate germ plasm for the production of hybrids improved with respect to various traits of economic importance, such as mushroom color, size, yield, growth rate, temperature optima, disease resistance, and the like. Furthermore, because the homokaryotic offspring can greatly predominate, the necessity for genetic screening may be eliminated. The heterokaryons present among spore offspring may not need to be screened out prior to using the homokaryotic offspring for breeding purposes.

An additional use of homokaryons of *Agaricus bisporus* is to observe whether genetic markers segregate jointly or independently at meiosis. Segregation usually cannot be observed in heterokaryotic offspring of this species. Analysis of segregation at multiple loci permits economically important trait loci to be located on genetic maps, associated with linked markers, followed through crosses and identified among offspring, and, if desired, cloned and sequenced. Because the present invention facilitates the production of homokaryons, it is an important adjunct to genetic mapping and genetic engineering in this species.

At this point, it should be understood that the initial material employed in the invention was not known to be a tetrasporic variety of *Agaricus bisporus*. In fact, no such variety was known to exist. Furthermore, there were strong indications, based upon morphological data, that the initial material did not belong to the species *Agaricus bisporus*. Moreover, as noted hereinabove, the literature available prior to the demonstration of the present invention indicates that trying to cross breed material of a four-spored Agaricus species with two-spored *Agaricus bisporus* was very likely to be unsuccessful. Specimens of the initial material have been collected from nature in Riverside County, Calif., USA, since November, 1989. These specimens are identified along with their dates of collection in Table I.

TABLE I

Specimens of *Agaricus bisporus* var. *burnettii*

| Specimen ID | Date of Collection | Specimen ID | Date of Collection |
|---|---|---|---|
| JB 2 | 10 Nov 1989 | JB 3 | Nov 1990 |
| JB 10 | Feb 1992 | JB 11 | Feb 1992 |
| JB 12 | Feb 1992 | JB 13 | Feb 1992 |
| JB 14 | Feb 1992 | JB 15 | Feb 1992 |
| JB 16 | Feb 1992 | JB 17 | Feb 1992 |
| JB 18 | Feb 1992 | JB 19 | Feb 1992 |
| JB 20 | Feb 1992 | JB 21 | Feb 1992 |
| JB 22 | Feb 1992 | JB 23 | Feb 1992 |
| JB 24 | Feb 1992 | JB 25 | Feb 1992 |
| JB 26 | Feb 1992 | JB 27 | Feb 1992 |
| JB 28 | Feb 1992 | JB 29 | Feb 1992 |
| JB 30 | Feb 1992 | JB 31 | Feb 1992 |
| JB 32 | Feb 1992 | JB 33 | Feb 1992 |
| JB 34 | Feb 1992 | JB 35 | Feb 1992 |
| JB 36 | Feb 1992 | JB 37 | Feb 1992 |
| JB 38 | Feb 1992 | JB 39 | Feb 1992 |
| JB 40 | Feb 1992 | JB 41 | Feb 1992 |
| JB 101 | 07 Mar 1992 | JB 102 | 07 Mar 1992 |
| JB 103 | 07 Mar 1992 | JB 104 | 07 Mar 1992 |
| JB 105 | 07 Mar 1992 | JB 106 | 07 Mar 1992 |
| JB 107 | 07 Mar 1992 | JB 108 | 07 Mar 1992 |
| JB 109 | 07 Mar 1992 | JB 110 | 07 Mar 1992 |
| JB 111 | 07 Mar 1992 | JB 112 | 07 Mar 1992 |
| JB 113 | 07 Mar 1992 | JB 114 | 07 Mar 1992 |
| JB 115 | 07 Mar 1992 | JB 116 | 07 Mar 1992 |
| JB 117 | 07 Mar 1992 | JB 118 | 08 Mar 1992 |
| JB 119 | 08 Mar 1992 | JB 120 | 08 Mar 1992 |
| JB 121 | 08 Mar 1992 | JB 122 | 08 Mar 1992 |
| JB 123 | 08 Mar 1992 | JB 124 | 08 Mar 1992 |
| JB 125 | 08 Mar 1992 | JB 126 | 08 Mar 1992 |
| JB 127 | 08 Mar 1992 | JB 128 | 08 Mar 1992 |
| JB 129 | 08 Mar 1992 | JB 130 | 08 Mar 1992 |
| JB 131 | 08 Mar 1992 | JB 132 | 09 Mar 1992 |
| JB 133 | 09 Mar 1992 | JB 134 | 09 Mar 1992 |
| JB 135 | 09 Mar 1992 | JB 136 | 09 Mar 1992 |
| JB 137 | 09 Mar 1992 | JB 138 | 09 Mar 1992 |
| JB 139 | 09 Mar 1992 | JB 140 | 09 Mar 1992 |
| JB 141 | 09 Mar 1992 | JB 142 | 09 Mar 1992 |
| JB 143 | 09 Mar 1992 | JB 144 | 09 Mar 1992 |
| JB 145 | 09 Mar 1992 | JB 146 | 09 Mar 1992 |
| JB 147 | 09 Mar 1992 | JB 148 | 09 Mar 1992 |
| JB 149 | 09 Mar 1992 | JB 161 | 13 Mar 1992 |
| JB 162 | 13 Mar 1992 | JB 163 | 13 Mar 1992 |
| JB 164 | 13 Mar 1992 | JB 165 | 13 Mar 1992 |
| JB 166 | 13 Mar 1992 | JB 155 | Apr 1992 |
| JB 157 | Apr 1992 | JB 167 | Apr 1992 |
| JB 168 | Apr 1992 | JB 169 | Apr 1992 |
| JB 171 | Apr 1992 | JB 172 | Apr 1992 |
| JB 173 | Apr 1992 | JB 174 | Apr 1992 |
| JB 175 | Apr 1992 | JB 176 | Apr 1992 |
| JB 177 | Apr 1992 | JB 178 | Apr 1992 |
| JB 179 | Apr 1992 | JB X | Apr 1992 |
| RWK 1840 | 07 Mar 1992 | RWK 1841 | 07 Mar 1992 |
| RWK 1842 | 07 Mar 1992 | RWK 1843 | 07 Mar 1992 |
| RWK 1844 | 07 Mar 1992 | RWK 1845 | 07 Mar 1992 |
| RWK 1846 | 07 Mar 1992 | RWK 1847 | 07 Mar 1992 |
| RWK 1848 | 07 Mar 1992 | RWK 1849 | 07 Mar 1992 |
| RWK 1850 | 07 Mar 1992 | RWK 1851 | 07 Mar 1992 |
| RWK 1852 | 07 Mar 1992 | RWK 1853 | 07 Mar 1992 |
| RWK 1854 | 07 Mar 1992 | RWK 1855 | 07 Mar 1992 |
| RWK 1856 | 07 Mar 1992 | RWK 1857 | 07 Mar 1992 |
| RWK 1858 | 07 Mar 1992 | RWK 1859 | 07 Mar 1992 |

TABLE I-continued

Specimens of *Agaricus bisporus* var. *burnettii*

| Specimen ID | Date of Collection | Specimen ID | Date of Collection |
|---|---|---|---|
| RWK 1860 | 07 Mar 1992 | RWK 1861 | 07 Mar 1992 |
| RWK 1862 | 07 Mar 1992 | RWK 1863 | 07 Mar 1992 |
| RWK 1864 | 07 Mar 1992 | RWK 1865 | 07 Mar 1992 |
| RWK 1866 | 07 Mar 1992 | RWK 1867 | 07 Mar 1992 |
| RWK 1868 | 07 Mar 1992 | RWK 1869 | 07 Mar 1992 |
| RWK 1870 | 07 Mar 1992 | RWK 1871 | 07 Mar 1992 |
| RWK 1872 | 07 Mar 1992 | RWK 1873 | 19 Mar 1992 |
| RWK 1874 | 19 Mar 1992 | RWK 1875 | 19 Mar 1992 |
| JB 191 | 10 Apr 93 | JB 192 | 10 APR 93 |
| JB 193 | 10 Apr 93 | JB 194 | 10 APR 93 |
| JB 195 | 10 Apr 93 | JB 196 | 10 APR 93 |
| JB 197 | 10 Apr 93 | JB 198 | 10 APR 93 |
| JB 199 | 10 Apr 93 | JB 200 | 10 APR 93 |
| JB 201 | 10 Apr 93 | JB 202 | 10 APR 93 |
| JB 203 | 10 Apr 93 | JB 204 | 10 APR 93 |
| JB 205 | 10 Apr 93 | JB 206 | 10 APR 93 |
| JB 207 | 10 Apr 93 | JB 208 | 10 APR 93 |
| JB 209 | 10 Apr 93 | JB 210 | 10 APR 93 |

For several of these field specimens, tissue cultures have been prepared. For the remainder, samples of viable spores have been preserved, and single- and multiple-spore cultures have been prepared from some of these samples. However, for many of these field specimens, no genetic, inteffertility, micromorphological, or cultural confirmation of identity has been made. Consequently, it is possible that some of the collections listed might actually represent taxa other than var. *burnettii*, although this number is unlikely to exceed a very small percentage.

The initial steps of the invention utilized germ plasm from these wild strains of Agaricus, now placed in the newly proposed, characteristically four-spored taxon *Agaricus bisporus* var. *burnettii*. Two of these heterokaryotic stocks (JB2 and JB3) were each preserved as multiple-spore samples which were prepared from the specimens collected from nature in Riverside County, Calif., between November, 1989 and November 1990. One heterokaryotic multi-spore culture, prepared from the JB2 sample, having the proposed taxonomic description of *Agaricus bisporus* var. *burnettii* and designated as JB2-ms (Accession No. 76072), has been deposited with the American Type Culture Collection under the terms of the Budapest Treaty on the International Recognition of the Deposit of Microorganisms for the Purposes of Patent Procedure and has been available to the scientific public upon request since the 2nd of May, 1990. Genotype data was obtained for the heterokaryotic cultures JB2-ms and JB3-ms. These strains have unique combinations of genetic markers as reported in Table II set forth hereinbelow.

TABLE II

Genotype Data on Stocks JB2 and JB3 of *Agaricus bisporus* from Riverside County, California, Based upon Multi-Spore Cultures

| Nuclear marker loci | JB2-ms Alleles | JB3-ms Alleles |
|---|---|---|
| P33N5 | 2/2 | 13/13* |
| P33N6 | 1/1 | 1/1 |
| P33N7 | 2/2 | _/_ |
| P33N10/1 | 3/3 | 3/5 |
| P33N10/2 | 6/6 | 2/6 |
| P33N13 | 5/5 | 5/5 |
| P33N14 | 8/8 | 5/7 |
| P33N18 | 1/1 | 1/1 |
| P33N25 | 8/8* | 3/4 |

TABLE II-continued

Genotype Data on Stocks JB2 and JB3 of
*Agaricus bisporus* from Riverside County,
California, Based upon Multi-Spore Cultures

| Nuclear marker loci | JB2-ms Alleles | JB3-ms Alleles |
|---|---|---|
| P4N6 | 4/4 | 4/4 |
| P4N27 | 1/1 | 1/2 |
| GPT | 1/1 | _/_ |
| ADH | 3/3 | 4/4 |
| PEP1 | 3/3 | 4/4 |
| PEP2 | 5/5[1] | 3/3 |
| BGLU | 3/5 | 5/5 |
| AAT | 3/3* | 1/1 |
| PGM | _/_ | 2/2 |
| EST | 2/2 | 3/3 |
| MPI | S/F | S/S |

[1]Heterozygosity was lost at PEP2 in JB2-ms; based on genotypic analysis of single-spore cultures of the JB2 stock, the parental genotype was 3/5.

The uniqueness of these genotypes may be seen by comparison to the table of cultivar and wild *Agaricus bisporus* genotypes presented in Appendix 2 of Kerrigan et at., "The California Population of *Agaricus bisporus* Comprises At Least Two Ancestral Elements," *Systematic Botany*, 18:123–136, (1993), hereby incorporated by reference. An asterisk (*) denotes a novel allele not previously observed in an extensive global sample of *Agaricus bisporus* stocks.

A similar pattern was observed when mitochondrial DNAs of JB2 and JB3 were subjected to restriction fragment analysis. Three mitochondrial fragments, B 1, B4b, and B13 were hybridized to EcoRI cut DNAs from JB2-ms and JB3-ms. The resulting patterns of fragments were compared to a world-side sample of over 200 strains of *Agaricus bisporus* var. *bisporus*. The JB2-ms and JB3-ms patterns observed with B13, B1 and B4b were observed respectively in 46 and 4, 2 and 1, and 0 and 0 var. *bisporus* isolates. As with the nuclear genotype data presented hereinabove, there were indications of similarity to *Agaricus bisporus* as well as indications of uniqueness, evolutionary isolation, and genetic divergence.

Other relevant characteristics of the JB2 stock include the fact that, unlike *Agaricus bisporus* var. *bisporus* mushrooms of the culture JB2-ms had a fertile lamellar margin (i.e., basidia were present there) and cheilcystidia were notably absent. Moreover, the size of the spores from the mushrooms of the JB2-ms culture, and from other samples of var. burnettii mushrooms, were significantly smaller than those of both wild and cultivated bisporic strains, now placed in the taxon known as *Agaricus bisporus* var. *bisporus*. A statistical analysis of the spore sizes was performed after obtaining length and width measurements on 10 to 60 spores from each of a total of 37 individual specimens from five different taxa (species or varieties). The mean of the length and width is provided for each specimen in Table III hereinbelow. Table IV sets forth a comparison of the overall means, and their standard deviations, for the five different taxa from which specimens were taken.

TABLE III

Spore Size Measurements of Five Agaricus Taxa

| Taxa | Mean Length (μ) | Mean Width (μ) |
|---|---|---|
| BISP | 6.45 | 4.97 |
| BISP | 6.95 | 5.49 |
| BISP | 6.73 | 5.24 |
| BISP | 6.38 | 5.13 |

TABLE III-continued

Spore Size Measurements of Five Agaricus Taxa

| Taxa | Mean Length (μ) | Mean Width (μ) |
|---|---|---|
| BISP | 6.64 | 5.31 |
| BISP | 7.24 | 5.55 |
| BISP | 7.08 | 5.84 |
| BISP | 6.79 | 4.99 |
| BISP | 6.83 | 5.18 |
| BISP | 7.20 | 5.33 |
| BISP | 6.94 | 5.55 |
| BISP | 7.02 | 5.52 |
| BISP | 6.75 | 5.48 |
| BISP | 7.09 | 5.52 |
| BISP | 6.45 | 5.10 |
| BISP | 7.58 | 5.74 |
| BURN | 5.56 | 4.49 |
| BURN | 5.37 | 4.27 |
| BURN | 5.47 | 4.44 |
| BURN | 5.74 | 4.47 |
| BURN | 5.51 | 4.56 |
| BRUN | 6.33 | 4.86 |
| BRUN | 6.34 | 4.88 |
| SBPR | 6.30 | 5.00 |
| SBPR | 5.83 | 4.55 |
| SBPR | 6.16 | 4.55 |
| SBPR | 6.03 | 4.65 |
| SBPR | 6.35 | 4.59 |
| SBPR | 5.99 | 4.59 |
| SBPR | 5.78 | 4.39 |
| SBPR | 6.34 | 4.68 |
| SBPR | 6.00 | 4.48 |
| SBPR | 6.08 | 4.50 |
| SBPR | 5.89 | 4.62 |
| SBPR | 6.08 | 4.50 |
| SBPR | 6.04 | 4.47 |
| SFLC | 6.33 | 4.86 |

Legend for Table III
BISP = *Agaricus bisporus* var. *bisporus*
BURN = *Agaricus bisporus* var. *burnettii*
BRUN = *Agaricus brunnescens*
SBPR = *Agaricus subperonatus*
SFLC = *Agaricus subfloccosus*

TABLE IV

Statistical Comparison Spore Sizes of Five Agaricus Taxa

| Taxa | Mean Length (μ) | (SD) | Mean Width (μ) | (SD) |
|---|---|---|---|---|
| BISP | 6.88 | 0.312 | 5.37 | 0.248 |
| BURN | 5.53 | 0.122 | 4.45 | 0.096 |
| BRUN | 6.34 | NA | 4.87 | NA |
| SBPR | 6.07 | 0.175 | 4.58 | 0.143 |
| SFLC | 6.33 | NA | 4.86 | NA |

Legend for Table IV
BISP = *Agaricus bisporus* var. *bisporus*
BURN = *Agaricus bisporus* var. *burnettii*
BRUN = *Agaricus brunnescens*
SBPR = *Agaricus subperonatus*
SFLC = *Agaricus subfloccosus*

Upon viewing the Tables III and IV, it should be clear that the spores taken from the var. *burnettii* strains were much smaller than the spores taken from specimens known to be *Agaricus bisporus* var. *bisporus*. The greatest mean spore length observed for var. *burnettii* fell 3.65 standard deviations (SD) below the grand mean for what is now known as *Agaricus bisporus* var. *bisporus*. The greatest mean spore width observed for var. *burnettii* fell 3.27 SD below the grand mean for what is now known as *Agaricus bisporus* var. *bisporus*. The least mean spore length observed for what is now known as *Agaricus bisporus* var. *bisporus* fell 6.97 SD above the grand mean for var. *burnettii*. The least mean spore width observed for what is now known as *Agaricus bisporus* var. *bisporus* fell 5.42 SD above the grand mean for var. *burnettii*. The difference in mean spore lengths for the two groups was equivalent to 4.33 SD, based upon the traditional *Agaricus bisporus* var. *bisporus* distribution, and equivalent to 11.07 SD, based on the var. *burnettii* distribution. The difference in mean spore widths for the two groups was equivalent to 3.71 SD, based upon the traditional *Agaricus bisporus* var. *bisporus* distribution, and equivalent to 9.58 SD, based on the var. *burnettii* distribution. Furthermore, without expressly detailing the difference, it is clear the hiatus in both spore length and spore width between the smallest *Agaricus bisporus* var. *bisporus* values and the largest var. *burnettii* values are substantially different when based upon either distribution. Thus, the new material did not fall within the existing circumscription of *Agaricus bisporus*.

Nevertheless, in view of certain similarities between the genotypic data for *Agaricus bisporus* and the genotypic data presented in Table II, it was deemed worthwhile to take the unusual step of performing interfertility testing between these new strains and strains of *Agaricus bisporus*. The tests were constructed (1) to determine whether hybrid heterokaryons could be formed in confrontation between homokaryons of *Agaricus bisporus* and those of the new tetrasporic stocks, and (2) to ascertain the heritability of the spore number trait in any hybrids that might be produced. With respect to the latter issue, some background data on the spore number traits exhibited by the stocks utilized in the experiment is in order. Accordingly, in Table V, the number of spores per basidium for several commercially cultivated bisporic strains were determined by conventional light microscopy techniques as discussed in detail hereinbelow. Each of these strains was cultured under locally standard industry conditions. Once the mushrooms produced began to sporulate abdundantly, the spore number data were obtained.

TABLE V

Spore Number Data on Certain *Agaricus bisporus* var. *bisporus*

| Trial # | Stock | Percentage of N-spored Basidia | | | |
|---|---|---|---|---|---|
| | | 4-spored | 3-spored | 2-spored | 1-spored |
| 1 | FS 40 | 0.0 | 0.7 | 98.3 | 1.0 |
| 2 | FS 25 | 0.0 | 9.0 | 89.7 | 1.3 |
| 3 | TV 2 | 1.0 | 4.3 | 95.7 | 0.0 |
| 4 | RWK 1547 | 0.0 | 1.0 | 98.7 | 0.3 |
| 5 | RWK 1634 | 0.0 | 3.0 | 97.0 | 0.0 |
| 6 | RWK 1646 | 0.0 | 5.7 | 94.3 | 0.0 |
| 7 | 303 | 0.0 | 0.0 | 100.0 | 0.0 |
| 8 | S381 | 0.0 | 5.3 | 94.0 | 0.7 |
| 9 | 56B | 0.3 | 9.7 | 87.0 | 3.0 |
| 10 | S600 | 0.0 | 0.0 | 92.7 | 7.3 |

Similarly, spore number data were obtained for a number of cultures of the new tetrasporic strains and are reported in Table VI. For the JB2 and JB3 stocks, spores were taken from the mushrooms found in nature and multi-spore cultures JB2-ms and JB3-ms were formed as noted hereinabove. For the other stocks noted in Table VI, cell tissue was obtained from each original mushroom and was regrown so as to form heterokaryotic tissue cultures.

TABLE VI

Spore Number Data on Certain *Agaricus bisporus* var. *burnettii*

| Trial # | Stock | Percentage of N-spored Basidia | | | |
|---|---|---|---|---|---|
| | | 5-spored | 4-spored | 3-spored | 2-spored |
| 1 | JB 2 | 0.0 | 99.0 | 1.0 | 0.0 |
| 2 | JB 3 | 1.7 | 92.3 | 6.0 | 0.0 |
| 3 | JB 102 | 2.0 | 97.7 | 0.3 | 0.0 |
| 4 | JB 104 | 0.0 | 95.0 | 14.3 | 0.7 |
| 5 | JB 105 | 0.0 | 92.7 | 7.0 | 0.3 |
| 6 | JB 106 | 0.0 | 100.00 | 0.0 | 0.0 |
| 7 | JB 107 | 0.0 | 92.0 | 7.3 | 0.7 |
| 8 | JB 108 | 0.0 | 95.0 | 5.0 | 0.0 |
| 9 | JB 109 | 0.0 | 53.0 | 41.3 | 5.7 |
| 10 | JB 110 | 0.0 | 96.7 | 3.3 | 0.0 |
| 11 | JB 111 | 0.0 | 72.0 | 27.0 | 1.0 |
| 12 | JB 117 | 0.0 | 54.0 | 38.0 | 8.0 |
| 13 | JB 118 | 0.0 | 93.0 | 6.0 | 1.0 |
| 14 | JB 121 | 0.3 | 92.0 | 7.3 | 0.3 |
| 15 | JB 123 | 0.0 | 96.0 | 4.0 | 0.0 |
| 16 | JB 125 | 0.3 | 88.0 | 11.7 | 0.0 |

Crosses were attempted as described hereinabove, between homokaryons from JB2 and known homokaryons from certain of the wild and cultivated, two-spored heterokaryotic breeding stocks of *Agaricus bisporus* as shown in Table V.

In Experiment 1, individual homokaryons from JB2 were each crossed with a homokaryon from a commercial, non-hybrid, white, two-spored *Agaricus bisporus* var. *bisporus* stock belonging to the genotypic class No. 2 as set forth in Royse and May, "Use of Isozyme Variation to Identify Genotypic Classes of *Agaricus brunnescens*" Mycologia 74:93–102 (1982), which is hereby incorporated by reference and maintained in the Sylvan Spawn Laboratory Incorporated ("Sylvan Spawn") culture collection under the Stock 303 designation as shown in Trial 7 of Table V.

In Experiment 2, individual homokaryons from JB2 were each crossed with a homokaryon from a wild, heterokaryotic, two-spored, white *Agaricus bisporus* var. *bisporus* stock, belonging to the genotypic class No. 36, as identified in Kerrigan and Ross, "Allozymes for a Wild *Agaricus bisporus* Population: New Alleles, New Genotypes," Mycologia 81:433–443 (1989), hereby incorporated by reference. This strain of *Agaricus bisporus* is maintained in the Sylvan Spawn culture collection and is designated as Stock R (also known as Stock RWK 1420).

In Experiment 3, individual homokaryons from JB2 and a different homokaryon taken from the same Stock R as employed in Experiment 2 were crossed.

In Experiment 4, individual homokaryons from JB2 were each crossed with a homokaryon from a pre-hybrid, heterokaryotic, two-spored, brown *Agaricus bisporus* var. *bisporus* stock. This strain of *Agaricus bisporus* is maintained in the Sylvan Spawn culture collection and is designated as Stock 56B as shown in Trial 9 of Table V.

In Experiment 5, an individual homokaryon (-s11) from JB2 was crossed with homokaryons (-h25, -h33, and -h12) from a hybrid, heterokaryotic, two-spored, brown *Agaricus bisporus* var. *bisporus* stock. This strain of *Agaricus bisporus* is maintained in the Sylvan Spawn culture collection and is designated as Stock S600 as shown in Trial 10 of Table V. Notably, stock S600 is the commercial horticultural variety of *Agaricus bisporus* claimed in U.S. Plant Pat. No. Plant 7,636.

For the convenience of the reader, a pedigree chart of three hybrids which are treated in subsequent experiments is presented in Table VII hereinbelow.

TABLE VII

Pedigrees of J81, J99, J102 and J154

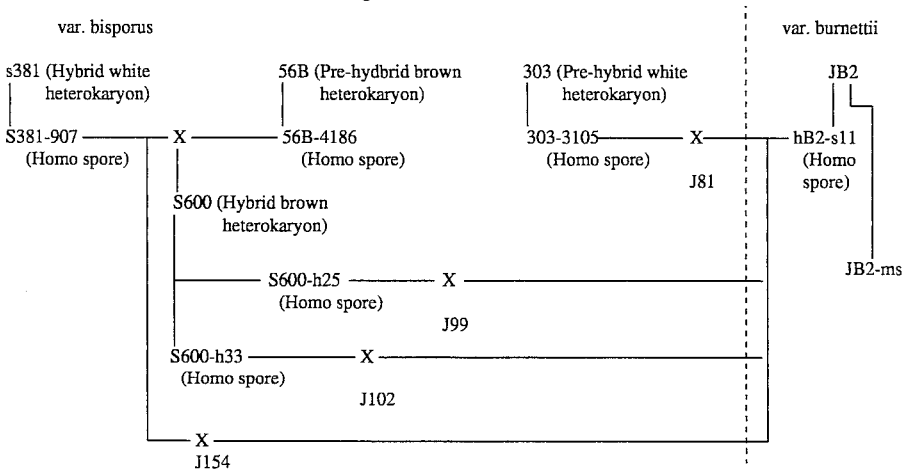

In accordance with commercial practice, the novel hybrid heterokaryons formed from each cross were transferred to grain culture, and then to compost culture, to permit the production of hybrid mushrooms. Mushrooms were produced in all crosses in all cases. These mushrooms have basidia which predominantly bear at least three spores as reported in Table VIII hereinbelow. The proportions of four-spored and other basidia were determined by light microscopy as discussed in Kerrigan and Ross, "Dynamic Aspects of Basidiospore Number in Agaricus,"*Mycologia*, 79(2), 204–215 (1987). Specifically, light microscopy was performed with a Nikon compound microscope with a 20x objective and 10x ocular. Lamellae were excised from the freshly harvested subject mushrooms and placed on a glass slide to form a dry mount. Observations were made immediately by transmitted light. Basidia were sampled by selecting an area of the lamella at random, and most or all basidia at the appropriate developmental stage within that visual field were scored. Successive fields were scored until one hundred (100) basidia had been scored. This was typically repeated on two additional lamellae to furnish a total sample of three hundred (300) basidia from each hybrid mushroom. Basidia which had aborted spores or asynchronous spore development were excluded from scoring, as were basidia so mature that one or more spores might have been discharged prior to observation.

TABLE VIII

Results of Individual Crosses Between the Four-Spored Stock JB2 and Various Two-Spored Stocks of *Agaricus Bisporus*

| Trial # | Homokaryon No. | 5-Spored | 4-Spored | 3-Spored | 2-Spored | Hybrid ID |
|---|---|---|---|---|---|---|
| Experiment 1 — Stock JB2 Crossed with Homokaryon -3105 of Stock 303 | | | | | | |
| 1 | s1 | 0.7 | 68.0 | 30.0 | 1.3 | J51 |
| 2 | s2 | 0.0 | 67.7 | 31.7 | 0.7 | J54 |
| 3 | s3 | 0.3 | 65.7 | 32.3 | 1.7 | J57 |
| 4 | s4 | 0.3 | 82.7 | 14.7 | 2.3 | J60 |
| 5 | s5 | 0.0 | 90.0 | 9.7 | 0.3 | J63 |
| 6 | s6 | 0.0 | 64.0 | 35.3 | 0.7 | J66 |
| 7 | s7 | 0.0 | 72.7 | 26.3 | 1.0 | J69 |
| 8 | s8 | 0.0 | 78.7 | 21.3 | 0.0 | J72 |
| 9 | s9 | 0.3 | 62.0 | 37.7 | 0.0 | J75 |
| 10[a] | s10 | 0.0 | 65.7 | 32.0 | 2.3 | J78 |
| 10[b] | s10 | 0.0 | 66.3 | 33.7 | 0.0 | J78 |
| 11 | s11 | 0.0 | 51.0 | 43.0 | 6.0 | J81 |
| Experiment 2 — Stock JB2 Crossed with Homokaryon -9559 of Stock R | | | | | | |
| 12 | s1 | 0.0 | 36.0 | 60.0 | 4.0 | J52 |
| 13 | s2 | 0.0 | 62.3 | 37.0 | 0.7 | J55 |
| 14 | s3 | 0.3 | 59.4 | 38.3 | 2.0 | J58 |
| 15 | s4 | 0.0 | 43.3 | 52.3 | 4.3 | J61 |
| 16 | s5 | 0.0 | 51.3 | 46.7 | 2.0 | J64 |
| 17 | s6 | 0.0 | 55.0 | 44.0 | 1.0 | J67 |
| 18 | s7 | 0.0 | 71.7 | 28.3 | 0.0 | J70 |
| 19 | s8 | 0.0 | 72.7 | 27.3 | 0.0 | J73 |
| 20 | s9 | 0.0 | 68.0 | 29.0 | 3.0 | J76 |
| 21 | s10 | 0.0 | 60.3 | 38.0 | 1.7 | J79 |
| 22 | s11 | 0.0 | 36.0 | 58.3 | 5.7 | J82 |
| Experiment 3 — Stock JB2 Crossed with Homokaryon -s5 of Stock R | | | | | | |
| 23 | s1 | 0.0 | 94.0 | 5.7 | 0.3 | J53 |
| 24 | s2 | 0.0 | 85.0 | 14.33 | 0.7 | J56 |
| 25 | s3 | 0.0 | 96.3 | 3.7 | 0.0 | J59 |
| 26 | s4 | 0.0 | 93.7 | 6.3 | 0.0 | J62 |
| 27 | s5 | 0.0 | 86.0 | 13.7 | 0.3 | J65 |
| 28 | s6 | 0.0 | 64.7 | 33.7 | 1.7 | J68 |
| 29 | s7 | 0.0 | 97.7 | 2.3 | 0.0 | J71 |
| 30 | s8 | 0.3 | 91.3 | 8.0 | 0.3 | J74 |
| 31 | s9 | 0.0 | 93.7 | 6.3 | 0.0 | J77 |
| 32 | s10 | 0.0 | 85.7 | 14.3 | 0.0 | J80 |
| 33 | s11 | 0.0 | 83.3 | 16.3 | 0.3 | J83 |
| Experiment 4 — Stock JB2 Crossed with Homokaryon -4186 of Stock 56B | | | | | | |
| 34 | s1 | 0.0 | 91.3 | 8.7 | 0.0 | J87 |
| 35 | s9 | 0.3 | 88.0 | 11.7 | 0.0 | J89 |

TABLE VIII-continued

Results of Individual Crosses Between the Four-Spored Stock JB2 and Various Two-Spored Stocks of *Agaricus Bisporus*

| | | Percentage of N-spored Basidia: | | | | |
|---|---|---|---|---|---|---|
| Trial # | Homokaryon No. | 5-Spored | 4-Spored | 3-Spored | 2-Spored | Hybrid ID |
| Experiment 5 — Stock S600 Crossed with Homokaryon -s11 of Stock JB2 | | | | | | |
| 36 | h25 | 0.0 | 25.0 | 65.0 | 10.0 | J99 |
| 37 | h33 | 0.0 | 40.0 | 54.0 | 6.0 | J102 |
| 38 | h12 | 0.0 | 37.0 | 60.0 | 3.0 | J108 |

Thus, based upon data collected and present evidence, it should be clear that at least 90 percent of the basidia produced in mushrooms of each hybrid strain are elevated to a higher spore number with respect to the two-spored condition prevailing in the bisporic parent. While the two-spored condition is not explicitly shown for Stock R in Table V, which is employed in Experiments 2 and 3 in Table VIII, it will be appreciated that tests have been performed on this stock which do show that it is, in fact, predominantly bisporic. Notably, the percentage of two-spored basidia has been reduced in the hybrid strains to less than 10 percent. Inasmuch as every first generation, intervarietal hybrid always expresses this elevated basidial spore number trait, the trait exhibits genetic dominance.

Furthermore, the percentage of homokaryons and heterokaryons produced by the spores of three of these first-generation intervarietal hybrids are shown in Table IX. Based upon the results presented in this Table, it is noted that the 54 to 57 percent production rate of homokaryons from the spores of hybrids J99 and J102 is more than five times the percentage production rate observed in any other normal bisporic strain, and is closer to 10 to 50 times the rate ordinarily obtained. Clearly, high proportions of homokaryons are produced by the spores of these hybrid mushrooms.

TABLE IX

Percentage of Homokaryons Found in Hybrids

| Hybrid ID | % Homokaryons | % Heterokaryons | No. of Spores Examined |
|---|---|---|---|
| J81 | 12.0 | 88.0 | 25 |
| J99 | 54.2 | 45.8 | 24 |
| J102 | 56.7 | 43.3 | 30 |

With respect to the rather low proportion of homokaryons shown for J81 in Table IX this result can be explained best by the existence of a greater mortality rate among homokaryotic spores. While spore mortality is high for both heterokaryotic and homokaryotic spores (80 to 99% is common), mortality may be higher among homokaryotic spores produced by certain heterokaryons. With particular reference to FIG. 2, empirical evidence for this fact is found in the article "Strategies for the Efficient Recovery of *Agaricus bisporus* Homokaryons" by Kerrigan et al. in *Mycologia*, 84(4), 575–579 (1992). Specifically, the growth rate frequency distribution curves for homokaryotic single spore isolates may be sharply truncated at the zero growth (inviability) point in contrast to those for heterokaryotic single spore isolates, suggesting that a disproportionately greater number of homokaryotic spores are inviable. The theoretical basis of this hypothesis is that secondary homothallism may favor the accumulation of recessive deleterious alleles, including those producing lethality in the haploid or homoallelic state.

To demonstrate that the present invention can utilize virtually any strain of var. *burnettii* as a tetraspofic parent in a cross to produce a hybrid heterokaryon having the elevated spore number trait, a series of intervarietal hybrid crosses were constructed using a very diverse selection of wild var. *burnettii* isolates. This sample, drawn from the list in Table I hereinabove, were collections that represented all of the known field sites and two different habitats from which isolates of var. *burnettii* were collected in March of 1992. The field sites are all within about 5 kilometers from each other. The geographical range of var. *burnettii* is not known.

The collections chosen for this experimental demonstration, the two var. *bisporus* to which they were crossed, the hybrid strain identifiers assigned to the new, resultant intervarietal hybrids, and the spore number data on the resultant hybrids are disclosed in Table X hereinbelow.

TABLE X

Results of Individual Crosses Between Various Four-Spored Stocks of *Agaticus bisporus* and Two Two-Spored Stocks of *Agaricus Bisporus*

| Sample | Homokaryon | Crossed with | Hybrid ID | Percentage of N-spored Basidia: 2-Spored | 3-Spored | 4-Spored |
|---|---|---|---|---|---|---|
| JB 105 | s3 | 303-3105 | J264 | 0 | 7 | 93 |
| JB 106 | s3 | 56B-4186 | J265 | 6 | 41 | 53 |
| JB 106 | s3 | 303-3105 | J266 | | no data available | |
| JB 106 | s9 | 56B-4186 | J267 | | no data available | |
| JB 108 | s4 | 56B-4186 | J268 | 1 | 17 | 82 |
| JB 108 | s4 | 303-3105 | J269 | 1 | 25 | 74 |
| JB 108 | s9 | 56B-4186 | J270 | 0 | 6 | 94 |

TABLE X-continued

Results of Individual Crosses Between Various Four-Spored Stocks
of *Agaticus bisporus* and Two Two-Spored Stocks of *Agaricus Bisporus*

| Sample | Homokaryon | Crossed with | Hybrid ID | Percentage of N-spored Basidia | | |
|---|---|---|---|---|---|---|
| | | | | 2-Spored | 3-Spored | 4-Spored |
| JB 108 | s9 | 303-3105 | J271 | 0 | 12 | 88 |
| JB 109 | s4 | 56B-4186 | J272 | 0* | 9 | 90 |
| JB 109 | s4 | 303-3105 | J273 | 3.5 | 39 | 57.5 |
| RWK 1841 | s1 | 56B-4186 | J274 | 4 | 45 | 51 |
| RWK 1841 | s1 | 303-3105 | J275 | 0 | 13 | 87 |
| RWK 1842 | s3 | 56B-4186 | J276 | 1 | 6 | 93 |
| RWK 1842 | s3 | 303-3105 | J277 | 3 | 44 | 53 |
| RWK 1842 | s4 | 56B-4186 | J278 | 0 | 6 | 94 |
| RWK 1842 | s4 | 303-3105 | J279 | 8 | 50 | 42 |
| RWK 1845 | s2 | 56B-4186 | J280 | 0 | 18 | 82 |
| RWK 1845 | s2 | 303-3105 | J281 | 3 | 49 | 48 |
| RWK 1855 | s1 | 56B-4186 | J282 | 1 | 59 | 40 |
| RWK 1855 | s1 | 303-3105 | J283 | no data available | | |
| RWK 1855 | s4 | 56B-4186 | J284 | 0 | 34 | 66 |
| RWK 1855 | s4 | 303-3105 | J285 | 4 | 44 | 52 |
| RWK 1856 | s8 | 56B-4186 | J286 | no data available | | |
| RWK 1856 | s8 | 303-3105 | J287 | no data available | | |
| RWK 1856 | s9 | 56B-4186 | J288 | no data available | | |
| RWK 1856 | s9 | 303-3105 | J289 | 2 | 38 | 60 |
| RWK 1857 | s5 | 56B-4186 | J290 | 5 | 74 | 21 |
| RWK 1857 | s5 | 303-3105 | J291 | 2 | 56 | 42 |
| RWK 1857 | s6 | 56B-4186 | J292 | 0 | 12 | 88 |
| RWK 1857 | s6 | 303-3105 | J293 | 4 | 46 | 50 |

*had 1 one-spored basidium

Spore number data on the parents of 303–3105 and 56B-4186 are provided hereinabove in Table V. Both are highly bisporic isolates of var. *bisporus*. Therefore, the dominant expression of the elevated spore number trait in the above intervarietal hybrids, seen most clearly as a reduction of the percentage of bisporic basidia to about 8 percent or less, confirms that most and perhaps all stocks of var. *burnettii* may be employed in the method of the present invention. A small number of crosses in the above test were unsuccessful. For example, JB 105-s1 mated only with 303–3105, and JB 106-s9 mated only with 56B-4186. This is consistent with mating type incompatibility, resulting from the sharing of a common allele at the mating type locus (MAT) by both homokaryons. This is a common occurrence in var. *bisporus* matings and does not reflect negatively on the method of the present invention. Six other homokaryons grew poorly on grain and were not useful in matings; again, this is also rather common among var. *bisporus* homokaryons. One of the tested stocks, RWK 1854, produced 2 such homokaryons, therefore no successful matings were obtained from this stock. This is believed to be a chance result, but no confirmation of this is available at the present time. However, the discovery that some stocks of *Agaricus bisporus* having tetrasporic ancestry are less desirable for the purposes of the present invention than others, or axe even unsuitable, would not materially affect the practice of the method of the present invention.

To demonstrate that virtually any strain of *Agaricus bisporus* var. *bisporus* can be used to form heterokaryons in crosses with var. *burnettii* homokaryons, the JB2 homokaryons -s8 and -s 1 were each crossed individually with three homokaryons of the off-white, pre-hybrid commercial Stock 8132, with two homokaryons of the golden-white, pre-hybrid commercial Stock 671, and with two homokaryons of Stock V1, a proprietary experimental hybrid between homokaryons of wild Stock RWK 1420. In all cases fertile heterokaryons were formed, and in about half of these trials, the yield equaled or exceeded that of the control, the high-yielding commercial strain S301. Three crosses between JB2 and JB3 homokaryons were also successful, resulting in fertile hybrid var. *burnettii* heterokaryons. In these experiments, the basidial spore numbers of the hybrid mushrooms were not determined.

It has also been determined that the elevated spore number trait which is found in the tetrasporic var. *burnettii* of *Agaricus bisporus* is a genetically-determined trait. Based upon results of the initial experiments provided in Table VIII, this trait is always inherited and expressed in the first hybrid generation. This is a hallmark of genetic dominance, and no other explanation satisfactorily explains the inheritance of this stable trait in all first-generation hybrids.

Formal genetic analysis was undertaken by preparing a series of 60 second-generation intervarietal hybrids. In these hybrids (J203 - J262), the first homokaryon was selected from among 12 prepared from spores of first-generation hybrid J102, and the second (non-intervarietal hybrid) homokaryon was from one of five strains of the bisporic var. *bisporus*. These five strains included:

| Homokaryon | Strain type |
|---|---|
| S381-907 | Hybrid White Cultivar |
| 8132-8010 | Pre-hybrid Off-white Cultivar |
| 303-3105 | Pre-hybrid White Cultivar |
| WQ-9525 | Pre-hybrid White Cultivar |
| RWK 1420-s5 | Wild Non-hybrid Coastal-Californian isolate |

The results of each cross are set forth in Table XI hereinbelow. Each of the five bisporic strains has been grouped as a separate experiment for the convenience of the reader.

TABLE XI

Results of Individual Crosses Between the Four-Spored Hybrid Stock J102 and Various Two-Spored Stocks of *Agaricus Bisporus*

| Trial | Homokaryon | Hybrid ID | 2-Spored | 3-Spored | 4-Spored |
|---|---|---|---|---|---|
| \multicolumn{6}{c}{Experiment A - Homokaryons from Hybrid Strain J102 Crossed with Homokaryon -907 of Stock S381} |
| 1 | s11 | J203 | — | NS | — |
| 2 | s12 | J208 | — | NF | — |
| 3 | s25 | J213 | 9 | 59 | 32 |
| 4 | s30 | J218 | — | NF | — |
| 5 | s15 | J223 | — | NS | — |
| 6 | s23 | J228 | 99 | 1 | 0 |
| 7 | s31 | J233 | — | NS | — |
| 8 | s40 | J238 | — | NF | — |
| 9 | s10 | J243 | 7 | 49 | 44 |
| 10 | s19 | J248 | — | NF | — |
| 11 | s22 | J253 | — | NS | — |
| 12 | s27 | J258 | — | NS | — |
| \multicolumn{6}{c}{Experiment B - Homokaryons from Hybrid Strain J102 Crossed with Homokaryon -8010 of Stock 8132} |
| 13 | s11 | J204 | 30 | 63 | 7 |
| 14 | s12 | J209 | — | NF | — |
| 15 | s25 | J214 | 2 | 52 | 46 |
| 16 | s30 | J219 | 53 | 41 | 6 |
| 17 | s15 | J224 | 36 | 63 | 1 |
| 18 | s23 | J229 | 29 | 63 | 8 |
| 19 | s31 | J234 | 20 | 69 | 11 |
| 20 | s40 | J239 | 23 | 57 | 20 |
| 21 | s10 | J244 | 10 | 60 | 30 |
| 22 | s19 | J249 | 18 | 67 | 15 |
| 23 | s22 | J254 | 14 | 68 | 18 |
| 24 | s27 | J259 | — | NF | — |
| \multicolumn{6}{c}{Experiment C - Homokaryons from Hybrid Strain J102 Crossed with Homokaryon -9525 of Stock WQ} |
| 25 | s11 | J205 | 96 | 4 | 0 |
| 26 | s12 | J210 | 90 | 10 | 0 |
| 27 | s25 | J215 | 26 | 63 | 11 |
| 28 | s30 | J220 | 23 | 61 | 6 |
| 29 | s15 | J225 | 84 | 16 | 0 |
| 30 | s23 | J230 | 54 | 33 | 3 |
| 31 | s31 | J235 | 87 | 13 | 0 |
| 32 | s40 | J240 | 79 | 21 | 0 |
| 33 | s10 | J245 | 2 | 53 | 45 |
| 34 | s19 | J250 | 91 | 9 | 0 |
| 35 | s22 | J255 | 60 | 40 | 0 |
| 36 | s27 | J260 | 98 | 2 | 0 |
| \multicolumn{6}{c}{Experiment D - Homokaryons from Hybrid Strain J102 Crossed with Homokaryon -s5 of Stock RWK 1420} |
| 37 | s11 | J206 | 43 | 56 | 1 |
| 38 | s12 | J211 | 77 | 23 | 0 |
| 39 | s25 | J216 | 16 | 62 | 22 |
| 40 | s30 | J221 | — | NF | — |
| 41 | s15 | J226 | 22 | 75 | 3 |
| 42 | s23 | J231 | 13 | 65 | 22 |
| 43 | s31 | J236 | 48 | 49 | 3 |
| 44 | s40 | J241 | 81 | 18 | 1 |
| 45 | s10 | J246 | 11 | 54 | 35 |
| 46 | s19 | J251 | 73 | 27 | 0 |
| 47 | s22 | J256 | 24 | 64 | 12 |
| 48 | s27 | J261 | — | NF | — |
| \multicolumn{6}{c}{Experiment E - Homokaryons from Hybrid Strain J102 Crossed with Homokaryon -3105 of Stock 303} |
| 49 | s11 | J207 | 96 | 4 | 0 |
| 50 | s12 | J212 | 90 | 10 | 0 |
| 51 | s25 | J217 | 12 | 59 | 29 |
| 52 | s30 | J222 | 27 | 65 | 8 |
| 53 | s15 | J227 | 99 | 1 | 0 |
| 54 | s23 | J232 | 87 | 13 | 0 |
| 55 | s31 | J237 | 95 | 5 | 0 |
| 56 | s40 | J242 | 70 | 26 | 4 |
| 57 | s10 | J247 | 6 | 59 | 35 |
| 58 | s19 | J252 | 93 | 7 | 0 |
| 59 | s22 | J257 | 84 | 16 | 0 |
| 60 | s27 | J262 | 100 | 0 | 0 |

NF = non-fruiting
NS = non-sporulating

Crosses to 8132-8010 and RWK 1420-s5 exhibited a range of elevated basidial spore numbers, but Mendelian segregation could not be clearly discerned. However, in crosses to 303-3105 and to WQ-9525, the spore-number trait of these second-generation intervarietal hybrids resolved clearly into two groups. Nine of the 12 crosses to 303-3105 had at least about 70% 2-spored basidia, while the remaining three crosses had about 27% or fewer 2-spored basidia. An inverse relationship was observed for 4-spored basidia in these 12 crosses. In the 12 crosses to WQ-9525, the cutoffs for percentage of 2-spored basidia that separated the two groups were greater than about 54% versus less than about 26%. The spore number values within each pair of crosses to WQ-9525 and 303-3105 were similar, indicating that the genetic makeup of the particular J102 homokaryon determined the expression of the trait in hybrid offspring. Thus, the data from the 24 crosses to WQ-9525 and 303-3105, in conjunction with the pedigree and spore number data presented above, clearly indicate that the elevated basidial spore number trait (in this experiment seen best as the replacement of 2-spored basidia with 3- and 4-spored ones) is controlled primarily by a single segregating genetic determinant. This proves that elevated spore number is a genetically determined trait. The gene locus that determines this trait has been provisionally named SNT. It further shows that the trait is expressed in the second, as well as the first, hybrid generation. Additional data below, presented in an example of the application of this technology to gene mapping, further support this assertion. Other data presented herein demonstrate that the elevated spore number trait exhibits genetic dominance.

Homokaryon S381-907 is a direct progenitor (essentially a gamete of the grandparent S381) of J102, and few of the back-crosses between J102 homokaryons and S381-907 developed normally, probably due to the effects of inbreeding. However, of those which did fruit and sporulate normally, two (J213 and J243) had about 32% and about 44% 4-spored basidia, respectively, and about 91% and about 93% at least 3-spored basidia, respectively. This ratio is not significantly different from the range of percentages given above for J102. Therefore, it is clear that the elevated spore number trait was retained in two back-crosses to the commercial var. *bisporus* cultivar S381. In contrast, a third back-cross (J228) had no four-spored basidia and 99 percent two-spored basidia. The influence of each individual J102 homokaryon on spore number in these three crosses was in complete agreement with observations on the crosses to Stocks 303 and WQ described hereinabove.

J213 and J243 are expected to have, on average, about 5/8 (62.5%) ancestry from S381, as opposed to the 50% that a first-generation hybrid, such as J154 (see Pedigree Chart hereinabove), will have. Ancestry, used quantitatively, is equivalent to the fraction of DNA inherited from a progenitor. However, because chromosomes assort independently and because of the infrequency of crossing over which occurs in *Agaricus bisporus* during meiosis, this percentage could actually be much higher (or lower) in any individual case. By using various breeding strategies and making additional generations of back-crosses, and by using genetic markers to select for homokaryons which have inherited more than 50% of their genome from the back-cross parent (e.g., S381), it is ultimately possible to construct one or a series of heterokaryons or homokaryons in which all of the genome, excluding a small chromosomal segment encompassing the spore number trait determining locus, comes from the back-cross parent. In other words, one or more strains having about 99% of their DNA from a var. *bisporus* strain like S381, and only about 1% from a var. *burnettii* strain like JB2, but expressing the elevated spore number trait originating in a var. *burnettii* strain, can be constructed using this method. The problem of inbreeding depression, which may be responsible for the high frequency of developmental problems in these back-crosses discussed hereinabove, can be ameliorated by back-crossing to sibling homokaryons of those from which the hybrid intermediates are descended. In other words, a different, sibling homokaryon of S381-907, when used in a cross between S381 and I102, will exhibit enough genetic differences from S381-907 to produce hybrids with less homozygosity than what is predicted to exist in the 12 back-crosses to S381-907. Homozygosity is an underlying cause of inbreeding depression.

At this point, it is noted that although the crossing of homokaryons is the preferred method of obtaining hybrids, it is also sometimes possible to cross a homokaryon with a heterokaryon or, in rare instances, to cross two heterokaryons. For example, some single-spore isolates from wild stocks of the tetrasporic var. *burnettii* of *Agaricus bisporus* are both self-fertile (and therefore heterokaryotic) and produce only white mushrooms (therefore lack a functional gene necessary for brown pigment production). When one such single-spore isolate (RWK 1845-sl) was paired with the homokaryon 56B-4186 of var. *bisporus* (which is not self-fertile, but which when mated always produces brown mushrooms because it carries a functional, dominant allele for brown pigment production), brown mushrooms were produced abundantly and exclusively as shown in Table XII. RWK 1845-sl is a single-spore isolate from field collection RWK 1845 of the tetrasporic vat. *burnettii* of *Agaricus bisporus*, collected within 3 kilometers of JB2 and JB3. Yield is the arithmetic mean of all replicates (usually three) of about 0.3 square feet each. The data shows that a mating between the var. *burnettii* heterokaryon and the var. *bisporus* homokaryon occurred and produced a high yielding brown hybrid.

TABLE XII

Demonstration of Heterokaryon-Homokaryon Mating

| Isolate(s) | Test | Yield (grams) | Color of Mushroom |
|---|---|---|---|
| RWK 1845-sl | 1 | 63 | White |
| | 2 | 235 | White |
| 56B-4186 | x* | 0 | |
| RWK 1845-sl × 56B-4186 | 1 | 280 | Brown |
| | 2 | 230 | Brown |
| Control (S600) | 1 | 214 | Brown |
| | 2 | 192 | Brown |

*will not colonize compost; never fruits unless mated

Continuing, the present invention may also include genetically engineering the tetrasporic trait into bisporic strains or stocks. That is, it is now possible to transform a diverse array of eukaryotic cells with exogenous DNA, thereby selectively incorporating individual genes determining economically important traits into the genetic background of an individual line or stock of the mushroom in question. It is now reasonable to believe that *Agaricus bisporus* may be transformed with respect to the spore number trait using recombinant DNA techniques.

The first step in this process involves locating (mapping) and isolating the DNA segment that encodes the gene locus responsible for expression of the "tetrasporic" trait in *Agaricus bisporus* var. *burnettii*. As noted hereinbelow, it has already been determined that a single genetic determinant, hereinafter called the Spore Number Trait locus (SNT), or possibly a cluster of linked loci within a single DNA segment, controls most or all of the expression of this trait in *Agaricus bisporus*, and that this locus lies very close to the PEP1 locus, as more specifically detailed hereinbelow. In Kerrigan et ai., "Meiotic Behavior and Linkage Relationships in the Secondarily Homothailic Fungus *Agaricus bisporus*," *Genetics*, 133:225-236 (1993), incorporated herein by reference, several allozyme and DNA RFLP and RAPD markers, including PEP2, R4-1, R4-3, PINt7, P1N31, HNI48, HNI50, P33N25, P33N25 and R18-6, have been mapped to within about 58.3, and to within as little as about 5.1 centiMorgans of PEP1, on Chromosome I of the nuclear genome. By quantifying the joint segregation of markers with SNT, the location of SNT can be pinpointed.

With this information, a chromosome walk is performed from one or more of these mapped DNA RFLP markers to the SNT locus. First, one may construct an ordered cosmid library of genomic DNA from *Agaricus bisporus*, using lambda phage as vector and maintaining the recombinant clones in *E. coli*. Ideally this library would contain only DNA from Chromosome I, which can be isolated by an alternating field electrophoresis technique such as contour-clamped homogeneous electrical field (CHEF) electrophoresis of whole-chromosome DNAs, following a preferred procedure discussed in Royer et al., "Electrophoretic Karyotype Analysis of the Button Mushroom *Agaricus bisporus*," *Genome*, 35:694-698 (1992), herein incorporated by reference, or a modification thereof. Overlapping homologous segments of DNA inserts in cosmids would permit the sequential ordering of the library via repeated hybridization of blots of clones in the library to probes incorporating ever more distant contiguous segments.

Such a walk will conventionally extend from a flanking marker through SNT to a flanking marker on the opposite side of SNT. Once this has been achieved, the approximate location of SNT can be estimated by comparing the recombinational distances between the two flanking markers and SNT, using the map data disclosed hereinbelow, with the cumulative lengths of all of the cosmid inserts in the spanned interval. Based on this estimate, the cosmid most likely to contain SNT can be identified. The inserted DNA from this cosmid could be subcloned, incorporated into a suitable vector, such as pUC18, and introduced into hyphae or protoplasts of a recipient *Agaricus bisporus* strain. The plasmid vector construct should provide positive selection for retention of plasmid in host, and for insertion of DNA of interest into a cloning site in the plasmid sequence. A number of other refinements might be incorporated into such a recombinant vector, depending upon which strategies are ultimately successful in transforming *Agaricus bisporus*, including detection of the recombinant DNA in the target cells, and whether homologous or non-homologous integration, or maintenance of the plasmid as a self-replicating cytoplasmic component, is preferred.

The recipient strain can be either a heterokaryon or a homokaryon, but will ordinarily carry no alleles for the "tetrasporic" trait; in other words, a bisporic strain will ordinarily be desired. Because the tetrasporic trait disclosed herein exhibits genetic dominance, the presence of the DNA of interest will be verifiable in any transformed strain because the tetrasporic trait will be expressed in mushrooms produced by a transformed homokaryon (or the hybrid produced by crossing a transformed homokaryon with another, compatible, bisporic homokaryon). This can be determined by fruiting the mushrooms and examining them microscopically. While this is an expensive and time-consuming assay, it is straightforward. If gene-dosage effects reduce expression of the novel DNA in a transformed hybrid, then homologous integration of the exogenous DNA to replace at least one copy of the (bisporic allele of the) SNT gene might be necessary.

DNA from cosmids increasingly distant from the most likely cosmid can also be used to transform the recipient strain. This series of experiments will continue until, at some point, a cosmid clone, or a subclone, is found which causes expression of the trait in a transformed hybrid.

At this point, the open reading frame (ORF) associated with the gene can be identified (through further subcloning and reconfirmation via transformation), sequenced, and studied. The subclone, in the appropriate vector, can be used to introduce the SNT gene controlling the trait into any bisporic strain of interest, without introducing any other trait from var. burnettii or losing any trait, other than bispory, form the target strain. From the sequence dam, it may be possible to understand the nature of the gene product and the mechanism by which it determines the pattern of basidiospore formation at the basidial apex. Finally, it may be possible to engineer new sequences which, when introduced, will have superior properties in terms of expression levels, the nature of the spore number pattern determined, or other improvements.

Turning to gene mapping, although heterokaryotic single-spore isolate progeny of *Agaricus bisporus* individuals are inbred, they exhibit little of the loss of parental heterozygosity that is characteristic of self-fertilization in most eukaryotes. As a result, Mendelian segregation of alleles is not observed in most single-spore offspring of var. *bisporus*, because most spores are heterokaryotic. To carry out gene mapping (in other words, to locate genes that control important phenotypic traits), it is necessary to determine whether alleles at two or more loci segregate jointly or independently, for example by characterizing the genotypes and/or phenotypes of a sufficient number of homokaryon offspring. By a sufficient number, it is meant that the number be great enough either to permit a sufficiently powerful statistical test of linkage, or to furnish a representative sample of individuals in pools of samples which are grouped into classes by trait. This number of homokaryons will vary inversely with the recombinational distance separating two loci, approaching infinity as the recombinational distance approached 50 percent, or conversely, becoming as few as 12–20 homokaryons when two loci are absolutely linked. It is normally possible to use every homokaryon of a basidiomycete species to furnish data used in gene mapping. Therefore, any method which increases the ability to obtain homokaryons from *Agaricus bisporus*, for example by increasing the fraction of homokaryons above the typical 3 percent and even above the exceptional about 10 percent, is of corresponding value to efforts to map genes in this species.

Once genes are mapped, it is possible to use linked flanking markers to follow them through crosses, which is of great value in efficiently breeding traits into or out of breeding stock and new hybrids. Thus, the present invention is of great value in this related aspect of mushroom breeding.

An example of gene mapping in *Agaricus bisporus* using the present invention is detailed hereinbelow. Specifically, with reference to the data pertaining to the second-generation crosses between the 12 homokaryons of J102 and the five var. *bisporus* homokaryons, the 12 J102 homokaryons were characterized genotypically at two allozyme marker loci, PEP1 and BGLU, in accordance with the method presented in Kerrigan and Ross, "Allozymes of a Wild *Agaricus bisporus* Population: New Alleles, New Genotypes," *Mycologia* 81:433–443 (1989). Genotypes for all 12 J102 homokaryons are presented in the Table XIII hereinbelow.

TABLE XIII

Genotype Data for J102 Homokaryons

| J102 | PEP1 | BGLU |
|---|---|---|
| s11 | S600-h33 | JB2-s11 |
| s12 | S600-h33 | JB2-s11 |
| s25 | JB2-s11 | JB2-s11 |
| s30 | JB2-s11 | JB2-s11 |
| s15 | S600-h33 | JB2-s11 |
| s23 | S600-h33 | JB2-s11 |
| s31 | S600-h33 | S600-h33 |
| s40 | — | JB2-s11 |
| s10 | JB2-s11 | JB2-s11 |
| s19 | S600-h33 | JB2-s11 |
| s22 | S600-h33 | JB2-s11 |
| s27 | S600-h33 | JB2-s11 |

Comparison of the eleven PEP1 data and spore number trait data from crosses to WQ-9525 and 303-3105, and also to S381-907, show a perfect correspondence, as shown in the two Punnett squares hereinbelow:

| | | PEP1 | | BGLU | |
|---|---|---|---|---|---|
| | | JB2-s11 | S600-h33 | JB2-s11 | S600-h33 |
| SNT1 | JB 2-s11 | 3* | 0 | 3* | 0 |
| | S600-h33 | 0 | 8* | 7 | 1* |

*parental classes

The ratio of parental to recombinant genotypes for the two loci, PEP1 and SNT is 11:0. While the dam are too few to permit a conventional chi-squared test of linkage, the direct probability of obtaining this result by chance is only about 3% $(=8/11)^{11}$. This exceeds the 5% error threshold conventionally used in genetic linkage analysis. This result provides preliminary evidence of tight linkage between the two loci PEP1 and SNT. Conversely, for the two loci BGLU and SNT, parentals do not even exceed recombinants, providing no evidence of linkage between these two loci.

In related experiments, it has also been determined that the loci PEP1 and PEP2 are tightly linked to the mating-type locus, provisionally named MAT. In S600, a commercial var. *bisporus* strain, a Punnet square for PEP2 and MAT gave 36 parentals:0 recombinants. This is highly significant evidence of tight linkage: chi-squared=36.0. From prior work, it is known that PEP1 and PEP2 are linked at a distance of about 6 percent recombination. Therefore, PEP1, PEP2, MAT, and SNT are all linked, apparently fairly tightly. Accordingly, each locus serves as a marker for the inheritance of traits determined by the other, linked loci. For example, PEP1 and PEP2 each mark both MAT and SNT, permitting these traits to be scored in homokaryons without necessitating the making of test-crosses, nor, in the case of SNT, the producing of crops of hybrid mushrooms followed by microscopic examination. Similarly, in a cross where both PEP1 and PEP2 were homozygous, and therefore uninformative, in the resulting hybrid, MAT and SNT would still serve as predictive markers for each other. The confidence level associated with predictions based on linked marker scores depends upon the degree of linkage existing between each pair of markers, which may vary somewhat from strain to strain, and which, even in the best studied cases, is still only approximately known for these loci.

It has been found that most hybrid intervarietal heterokaryons resulting from crosses between the tetrasporic var. *burnettii* and the bisporic var. *bisporus* of *Agaricus bisporus* tend to produce mushrooms in a shorter period of time than do isolates of var. *bisporus*. Specifically, after the casing soil layer is applied to compost which is fully colonized by the mushroom mycelium, mushrooms on intervarietal hybrid strains develop and are ready for harvest in fewer days than do mushrooms on var. *bisporus* strains. Additionally, it appears that colonization of the compost by the mycelium of the intervarietal hybrid strain is, in many cases, sufficiently vigorous to permit application of the casing layer one or more days earlier than what is customary for strains of var. *bisporus*, without resulting in a yield reduction. Both of these advantages may be combined to further shorten the duration of the crop cycle. Any such shortening of the crop cycle increases the number of crops that can be produced in a mushroom farm in a fixed period of time, which increases profitability of the farm. This crop cycle is, in part, under the control of the grower, rather than the mushroom, so the meaningful commercial comparison between strains must also be based upon the yield of mushrooms when different spawn to case intervals are imposed. The acceleration of the life cycle also represents an advantage in experimental breeding programs by permitting more rapid progress.

A test for early fruiting was performed as indicated generally hereinabove. In the test, three intervarietal hybrids, J81 (JB2-s11×303-3105), J82 (JB2-s11×RWK 1420-9559), and J83 (JB2-s11×RWK 1420-s5), and one commercial control, S130 (commercial hybrid var. *bisporus* strain), were employed. Each of the hybrids was cased with soil except one J83 (peat) which was cased in peat. No peat control was furnished. The results of this test are disclosed in Table XlV hereinbelow.

TABLE XIV

Results of Early Fruiting Test

| Hybrid or Control ID | Spawn run (days) | Case to Pick (days) | Yield (grams) | Yield (% of control) |
|---|---|---|---|---|
| J81 | 8 | 14.0 | 4116 | 113.0 |
| J82 | 8 | 14.3 | 4282 | 117.6 |
| J83 | 8 | 14.0 | 3828 | 105.1 |
| S130 (Control) | 8 | 15.8 | 3642 | 100.0 |
| Intervarietal hybrid advantage | | 1.7 days | | 11.9% |
| J81 | 10 | 15.7 | 3938 | 85.0 |
| J82 | 10 | 13.2 | 3736 | 80.7 |
| J83 | 10 | 13.0 | 3869 | 83.5 |
| S130 (Control) | 10 | 15.3 | 4631 | 100.0 |
| Intervarietal hybrid advantage | | 1.3 days | | −16.9% |
| J83 | 13 | 12.7 | 4315 | 102.1 |
| J83 (peat) | 13 | 12.5 | 4734 | (112.0) |
| S130 (Control) | 13 | 15.0 | 4227 | 100.0 |
| Intervarietal hybrid advantage | | 2.3 days | | 2.1% |

Overall speed advantage for intervarietal hybrids in all three spawn run durations was ca 1.7 days. Data are means of six replicates, each having about 0.25 square meters of cropping surface. The median yields (not shown) for all treatments and controls were not significantly different at the 95% confidence level. Thus, it can be concluded from these data that (1) the crop is ready for harvest almost 2 days earlier, on average, in the case of three intervarietal hybrids relative to the commercial var. *bisporus* control; and (2) the average yield is comparable between the experimental and control strains. It is also appears that the performance difference of the intervarietal hybrid as compared to the commercial var. *bisporus* control may tend to favor the intervarietal hybrids at the shortest spawn run durations.

Furthermore, the data presented hereinbelow indicate that intervarietal hybrids between the tetrasporic var. *burnettii* and the bisporic var. *bisporus* of *Agaricus bisporus* have yields which are often as high as or somewhat higher than the best performing commercial var. *bisporus* hybrids. This is unexpected because in evaluating the results of over 3,000 attempted matings between homokaryons of var. *bisporus*, the production of a novel hybrid capable of achieving this level of performance is almost unprecedented. Evidence of the frequently superior yield performance of the intervarietal hybrids as a group is presented in Table XIV hereinabove and Tables XV hereinbelow.

TABLE XV

Results of First Series of J-series Hybrid Yield Tests:

| Hybrid or Control ID | Cross: | Case to pick (days) | Yield: (grams) | Yield (% of control) |
|---|---|---|---|---|
| First group: (chamber) | | | | |
| S600 | (Control) | | 3768 | 100 |
| A93 | (Secondary control) | | 3820 | |
| J81 | JB2-s11 × 303-3105 | 2 | 4514 | 119.8 |
| J60 | JB2-s4 × 303-3105 | 2 | 4863 | 129.0 |
| J72 | JB2-s8 × 303-3105 | 1 | 4469 | 118.6 |
| First group: (mine) | | | | |
| S600 | (Control) | | 3658 | 100 |
| S381 | (Secondary control) | | 3449 | |
| J81 | JB2-s11 × 303-3105 | 3–4 | 4050 | 110.7 |

TABLE XV-continued

Results of First Series of J-series Hybrid Yield Tests:

| Hybrid or Control ID | Cross: | Case to pick (days) | Yield: (grams) | Yield (% of control) |
|---|---|---|---|---|
| J82 | JB2-s11 × 1420-9559 | 3–4 | 3981 | 108.8 |
| J83 | JB2-s11 × RWK 1420-s5 | 3–4 | 3962 | 108.3 |
| J60 | JB2-s4 × 303-3105 | 3–4 | 4265 | 116.6 |
| J72 | JB2-s8 × 303-3105 | 2–3 | 3311 | 90.5 |
| Second group: (mine) | | | | |
| S600 | (Control) | | 3613 | 100 |
| J56 | JB2-s2 × RWK 1420-s5 | 1 | 3530 | 97.7 |
| J57 | JB2-s3 × 303-3105 | 1 | 3705 | 102.5 |
| J61 | JB2-s4 × 1420-9559 | 1 | 3668 | 101.5 |
| J76 | JB2-s9 × 1420-9559 | 1 | 3897 | 107.9 |
| J80 | JB2-s10 × RWK 1420-s5 | 2 | 4311 | 119.3 |
| Third group (mine): | | | | |
| S600 | (Control) | | 3650 | |
| S381 | (Secondary control) | | 3888 | |
| J75 | JB2-s9 × 303-3105 | 1 | 4111 | 112.6 |
| J51 | JB2-s1 × 303-3105 | 1 | 4062 | 111.3 |
| J71 | JB2-s7 × RWK 1420-s5 | 0 | 2706 | 74.1 |
| J58 | JB2-s3 × 1420-9559 | 2 | 4525 | 124.0 |
| Fourth group (mine): | | | | |
| S600 | (Control) | | 4310 | |
| J52 | JB2-s1 × 1420-9559 | 1 | 4963 | 115.2 |
| J64 | JB2-s5 × 1420-9559 | 0–1 | 3212 | 74.5 |
| J79 | JB2-s10 × 1420-9559 | 1 | 3553 | 82.4 |
| J77 | JB2-s9 × 1420-s5 | 1 | 4441 | 103.0 |

TABLE XVI

Semi-finalist Yield Test Series: J-series Hybrids

| Hybrid or Control ID | Cross | Case to pick: (days) | Yield (grams) | Yield (% of control) |
|---|---|---|---|---|
| First group | | | | |
| S130 | (Control) | 16.3 | 3400 | 100.0 |
| J90 | JB2-s11 × S600-h1 | 13.0 | 3787 | 111.4 |
| J105 | JB2-s11 × S600-h2 | 13.3 | 4295 | 126.3 |
| J104 | JB2-s11 × S600-h3 | 13.7 | 4708 | 138.5 |
| J114 | JB2-s11 × S600-h20 | 13.5 | 4635 | 136.3 |
| J116 | JB2-s11 × S600-h31 | 13.8 | 3905 | 114.9 |
| J154 | JB2-s11 × S381-907 | 12.8 | 3572 | 105.1 |
| Second group | | | | |
| S130 | (Control) | 16.0 | 3571 | 100.0 |
| J108 | JB2-s11 × S600-h12 | 13.2 | 4689 | 131.3 |
| J117 | JB2-s11 × S600-h35 | 13.7 | 4678 | 131.0 |
| J119 | JB2-s11 × S600-h37 | 13.7 | 4582 | 128.3 |
| J120 | JB2-s11 × S600-h38 | 13.0 | 5018 | 140.5 |
| J121 | JB2-s11 × S600-h42 | 14.0 | 4514 | 126.4 |
| J125 | JB2-s11 × S600-h49 | 13.0 | 4740 | 132.7 |
| Third group | | | | |
| S130 | (Control) | 15.7 | 4586 | 100.0 |
| J91 | JB2-s11 × S600-h5 | 13.8 | 3922 | 85.5 |
| J92 | JB2-s11 × S600-h7 | 13.2 | 4066 | 88.7 |
| J96 | JB2-s11 × S600-h21 | 13.2 | 4005 | 87.3 |
| J100 | JB2-s11 × S600-h28 | 13.0 | 4450 | 97.0 |
| J102 | JB2-s11 × S600-h33 | 13.0 | 4560 | 99.4 |
| Fourth group | | | | |
| S130 | (Control) | 15.7 | 4594 | 100.0 |
| J95 | JB2-s11 × S600-h17 | 13.3 | 4663 | 101.5 |
| J97 | JB2-s11 × S600-h22 | 13.5 | 4454 | 97.0 |
| J109 | JB2-s11 × S600-h13 | 13.7 | 4783 | 104.1 |
| J113 | JB2-s11 × S600-h19 | 13.7 | 4876 | 106.1 |
| J118 | JB2-s11 × S600-h36 | 13.7 | 4586 | 99.8 |
| J89 | JB2-s9 × 56B-4186 | 13.2 | 4349 | 94.7 |

TABLE XVI-continued

| | Semi-finalist Yield Test Series: J-series Hybrids | | | |
|---|---|---|---|---|
| Hybrid or Control ID | Cross | Case to pick: (days) | Yield (grams) | Yield (% of control) |
| J156 | JB2-s11 × WQ-9525 | 15.8 | 3700 | 80.5 |
| | Avg. | 2.5 | | 106.6% |

In summary, the J-series hybrids, although picked 2.5 days earlier, on average, yielded 6.6 percent more, on average, than the best performing commercial control strain. The two to three day reduction in the case to pick interval represents a 5.7 to 8.6 percent reduction in cycle time in a commercial tray-based cropping room leading to a proportional increase in profitability.

Based upon the foregoing disclosure, it should now be apparent that crossbreeding a four-spored *Agaricus bisporus* mushroom, the spores of which are homokaryotic, and a two-spored mushroom of the same species, as described herein, will carry out the objects set forth hereinabove. Although the crossing of homokaryons is the preferred method of obtaining hybrids, it is also possible to cross a homokaryon with a heterokaryon or, in rare instances, to cross two heterokaryons. Thus, while homokaryons have been described throughout the specification, it should be understood that either homokaryons or heterokaryons, in any combination, may be employed (see Table XII). It is also possible to produce hybrids of *Agaricus bisporus* in less fully-defined situations in which mixtures of spores, protoplasts, or hyphal fragments are allowed to germinate or regenerate in mass cultures of uncertain ploidy, from which hybrid heterokaryons may subsequently be selected.

Moreover, it is also noted that the hybrids described hereinabove were eminently suitable for the production of mushroom spawn and other inocula. Accordingly, it will be understood that mushrooms produced by the hybrid heterokaryons of the present invention, as well as the commercial products incorporating the heterokaryons or homokaryons, or other processes or products which utilize the heterokaryons or homokaryons, are within the scope of the present invention. Spawn is one such commercial product.

Still further, it will be appreciated that the present invention does not necessarily relate to the intervarietal hybrid stocks. The crossing of two intravarietal stocks of *Agaricus bisporus* var. *burnettii* is also envisioned as falling within the scope of the present invention. It is also to be understood that any variations evident fall within the scope of the claimed invention and thus, the selection of specific crossbreeding techniques, and sources of and utilization of homokaryons or heterokaryons can be determined without departing from the spirit of the invention herein disclosed and described. Therefore, it is to be understood that other means of recombining genes, such as by genetic engineering, using recombinant DNA technology, may also be employed for the present invention. Thus, the scope of the invention shall include all modifications and variations that may fall within the scope of the attached claims.

We claim:

1. A method for the production of homokaryons from breeding stock of the mushroom *Agaricus bisporus* comprising the steps of: providing a first strain of *Agaricus bisporus* having tetrasporic ancestry and carrying at least one gene which determines the trait for production of mushrooms which produce basidia, among which basidia bearing at least three spores predominate; and crossing said first strain with at least a second strain of *Agaricus bisporus* to form at least one hybrid heterokaryotic culture, said at least one hybrid heterokaryotic culture being capable of producing mushrooms, the basidia of which predominantly bear at least three spores, at least 10 percent of said spores being homokaryotic.

2. Homokaryons carrying at least one gene which determines the trait for the production of mushrooms which produce basidia, among which basidia bearing at least three spores predominate, produced from spores on hybrid mushrooms and their descendants, said mushrooms formed by providing a first strain of *Agaricus bisporus* with tetrasporic ancestry and carrying at least one gene that determines the trait for production of mushrooms which produce basidia, among which basidia bearing at least three spores predominate; and crossing said first strain with at least a second strain of *Agaricus bisporus* to form at least one hybrid heterokaryotic culture; said at least one hybrid heterokaryotic culture being capable of producing said hybrid mushrooms and their homokaryotic descendants which carry said at least one gene.

3. Heterokaryons, and their inbred and outcrossed descendants, carrying at least one gene which determines the trait for the production of mushrooms which produce basidia, among which basidia bearing at least three spores predominate, produced from a cross between at least two strains of *Agaricus bisporus*, at least one of said strains having tetrasporic ancestry and carrying at least one gene which determines the trait for production of mushrooms which produce basidia, among which basidia bearing at least three spores predominate.

4. Inocula incorporating heterokaryons and their inbred and outcrossed descendants of claim 3.

5. Spawns incorporating heterokaryons and their inbred and outcrossed descendants of claim 3.

6. Mushrooms produced by heterokaryons and their inbred and outcrossed descendants of claim 3.

7. A method for the production of vigorous hybrid strains of *Agaricus bisporus* comprising the step of combining genetic material originating from a stock of *Agaricus bisporus* having tetrasporic ancestry and carrying at least one gene which determines the trait for production of mushrooms which produce basidia, among which basidia bearing at least three spores predominate, with genetic material from at least a second *Agaricus bisporus* stock.

8. The method, according to claim 7, wherein said vigorous hybrid strains fruit earlier following casing than commercial strain S600.

9. The method, according to claim 7, wherein said vigorous hybrid strains produce mushrooms at least as abundantly as commercial strain S600.

10. The method, according to claim 7, wherein said vigorous hybrid strains and commercial strain S130 may be cased earlier than thirteen days, said hybrid strains producing mushrooms at least as abundantly as commercial strain S130.

* * * * *

UNITED STATES PATENT AND TRADEMARK OFFICE
CERTIFICATE OF CORRECTION

PATENT NO.   : 5,563,317
DATED        : October 8, 1996
INVENTOR(S)  : Kerrigan et al.

It is certified that error appears in the above-identified patent and that said Letters Patent is hereby corrected as shown below:

Claim 2, column 30, line 21, insert the word "hybrid" between the words "said" and "mushroom".

Signed and Sealed this

Fifteenth Day of April, 1997

Attest:

BRUCE LEHMAN

Attesting Officer    Commissioner of Patents and Trademarks